US007923000B2

(12) United States Patent
Chen et al.

(10) Patent No.: US 7,923,000 B2
(45) Date of Patent: Apr. 12, 2011

(54) METHODS OF DETERMINING EFFICACY OF TREATMENTS OF INFLAMMATORY DISEASES OF THE BOWEL

(75) Inventors: Ker-Sang Chen, West Chester, OH (US); John Kevin Collins, Cork (IE); Barry Pius Kiely, Cork (IE); Fangyi Luo, Mason, OH (US); Liam Diarmuid O'Mahony, Cork (IE); Ross Peter Phillipson, Middlesex (GB); Fergus Shanahan, Cork (IE)

(73) Assignee: The Procter & Gamble Company, Cincinnati, OH (US)

( * ) Notice: Subject to any disclaimer, the term of this patent is extended or adjusted under 35 U.S.C. 154(b) by 475 days.

(21) Appl. No.: 10/810,358

(22) Filed: Mar. 26, 2004

(65) Prior Publication Data

US 2004/0228837 A1     Nov. 18, 2004

Related U.S. Application Data

(63) Continuation-in-part of application No. 10/404,512, filed on Apr. 1, 2003, now abandoned.

(51) Int. Cl.
| | |
|---|---|
| *A61K 49/00* | (2006.01) |
| *A01N 63/00* | (2006.01) |
| *A23K 1/18* | (2006.01) |
| *A23C 9/20* | (2006.01) |
| *C12Q 1/02* | (2006.01) |
| *C12Q 1/00* | (2006.01) |

(52) U.S. Cl. ............ 424/9.2; 424/93.1; 424/93.4; 426/2; 426/71; 426/29; 426/4

(58) Field of Classification Search ........................ None
See application file for complete search history.

(56) References Cited

U.S. PATENT DOCUMENTS

| 5,853,697 A | 12/1998 | Strober et al. |
| 2005/0106133 A1 | 5/2005 | Zink et al. |

FOREIGN PATENT DOCUMENTS

| EP | 0508701 B1 | 10/1992 |
| EP | 0862863 B1 | 9/1998 |
| EP | 1312667 A1 | 5/2003 |
| WO | WO 94/04180 A2 | 3/1994 |
| WO | WO 94/04180 A3 | 3/1994 |
| WO | WO 00/41707 A1 | 7/2000 |
| WO | WO 00/42168 A2 | 7/2000 |
| WO | WO 02/083879 A2 | 10/2002 |
| WO | WO 03/010297 A1 | 2/2003 |
| WO | WO 03/010298 A1 | 2/2003 |
| WO | WO 03/010299 A1 | 2/2003 |

OTHER PUBLICATIONS

Papadakis et al. 2000. Ann Rev Med. 51:289-298.*
Vignali DAA. 2000. Journal of Immunological Methods 243:243-255.*
Thompson et al 1999. Gut. 45/Suppl II:II43-II47.*
Whiteside 2003. Chapter 61 in The Cytokine Handbook, vol. II, 4th edition (pp. 1384-1386 enclosed).*
www.invitrogen.com/content.cfm?pageid+11317&CID=KNC-GOOGLE&s_kwcid=..., downloaded May 20, 2007.*
Togawa et al. 2002 Am J. Physiol, Gastrointestinal Liver Physiol 283:G187-G195.*
Blumberg et al. 1999. Current Opinion in Immunology 11:648-656.*
Vilcek 2003. Chapter 1 in "The Cytokine Handbook" vol. I, 4th edition (p. 6, enclosed).*
Bing et al. 1998. World J Gastroenterology 4:252-255.*
O'Gorman et al. 2008. Handbook of Human Immunology, 2nd edition, pp. 154 and 155.*
Hart et al. 2003. J. Clin Gastroent 36:111-9).*
Grundmann et al. 2010. J. Gastroenterology and Hepatology 25:691-699.*
Stallmach et al., "Induction and Modulation of Gastrointestinal Inflammation", Trends Immunology Today, Oct. 1998, vol. 19 No. 10 pp. 438-441.
Marteau et al., "Potential of Using Lactic Acid Bacteria for Therapy and Immnunomodulation in Man", FEMS Microbiology Reviews 12 (1993) 207-220.
Fergus Shanahan, "The Intestinal Immune System", Physiology of the Gastrointestinal Tract, Third Edition, 1994.
Schmitt et al., "The Immunostimulatory Function of IL-12 in T-Helper-Cell Development and Its Regulation by TGF-B, IFN-y and IL-4",Chem Immunet Basel Karger, 1997, vol. 68, pp. 70-85.
Panwala et al., "A Novel Model of Inflammatory Bowel Disease: Mice Deficient for the Multiple Drug Resistance Gene, mdrla, Spontaneously Develop Colitis", The American Association of Immunologists, 1998, The Journal of Immunology, 1998 161: 5733-5744.
O'Mahony et al., "Probiotic Impact on Microbial Flora, Inflammation and Tumour Development in IL-10 Knockout Mice", Aliment Pharmacol Ther 2001: 15: 1219-1225.
Medaglini et al., "Mucosal and Systemic Immune Responses to a Recombinant Protein Expressed on the Surface of the Oral Commensal Bacterium Streptococcus gordonii after oral colonization", Proc. Natl. Acad. Sci. USA vol. 92, pp. 6868-6872, Jul. 1995 Medical Sciences. Charteris et al, "Antiobiotic Sysceptibility of Potentially Probiotic Bifidobacterium Isolates From the Human Gastrointestinal Tract", Letters in Applied Microbiology 1998, 26, 333-337.
McGee et al., "A Synergistic Relationship Between TNF-x, IL-1B, and TGF-B1 on IL-6 Secretion by the IEC-6 Intestinal Epithelial Cell Line", Immunology 1995 86 6-11.
Bouhnik et al., "Effects of Bifidobacterium SP Fermented Milk Ingested With or Without Inulin on Colonic Bifidobacteria and Enezymatic activities in Healthy Humans" European Journal of Clinical Nutrition (1996) 50, 269-273.
Charteris et al., "Development and application of an In Vitro Methodology to Determine the Transit Tolerance of Potentially Probiotic *Lactobacillus* and *Bifidobacterium* Species in the Upper Human Gastrointestinal Tract" Journal of Applied Microbiology 1998, 84, 759-768-XP 000929203.
Charteris et al., "Antiobiotic Susceptibility of Potentially Probiotic *Bifidobacterium* Isolates from the Human Gastrointestinal Tract, "Letters of Applied Microbiology 1998, 26, 333-337.

(Continued)

*Primary Examiner* — Shulamith H Shafer
(74) *Attorney, Agent, or Firm* — Cynthia L. Clay; Kim William Zerby

(57) ABSTRACT

Novel methods of determining efficacy of a treatment of inflammatory diseases of the bowel in mammals are provided. The methods are of use in screening and determining the efficacy of treatments of inflammatory diseases of the bowel, and for determining the efficacy response of individual sufferers of inflammatory diseases of the bowel to a given regime. Kits for carrying out the method are also provided.

21 Claims, 4 Drawing Sheets

OTHER PUBLICATIONS

Charteris et al., "Selective Detection, Enumeration and Identification of Potentially Probiotic *Lactobacillus* and *Bifidobacterium* Species in Mixed Bacterial Populations", International Journal of Food Microbiology 35 (1997) 1-27.

Chevalier et al., "Detection of *Bifidobacterium* Species by Enzymatic Methods", Journal of Applied Basteriology 1990, 68, 619-624.

Collins et al., "Selection of Problotic Strains for Human Applications", In. Dairy Journal 8 (1998) 487-490.

Gibson et al., "Dietary Modulation of the Human Gut Microflora Using Prebiotics", Journal of Nutrition, (1998) 80. Suppl. 2 S209-S212.

Charteris et al., "Effect of Conjugated Bile Salts on Antibiotic Susceptibility of Bile Salt-Tolerant *Lactobacillus* and *Bifidobacterium* Isolates", Journal of Food Protection vol. 63, No. 10, 2000, pp. 1369-1376.

Groux et al., "Regulatory T Cells and Inflammatory Bowel Disease", Viewpoint Immunology Today Oct. 1999.

Brandtzaeg et al., "Immunopathology of Human Inflammatory Bowel Disease", Springer Seminars in Immunopathology (1997) 18: 555-589.

Chauviere et al., Adhension of Human *Lactobacillus Acidophilus* Strain LB to Human Enterocyte-like Caco-2 Cells, Journal of General Microbiology (1992), 138,1689-1696.

Cicco et al., "Inducible Production of Interleukin-6 by Human Polymorphonuclear Neutrophils: Role of Granulocyte-Macrophage Cology-Stimulating Factor and Tumor Necrosis Factor-Alpha", 1990 The American Society of Hematology, Blood, vol. 75, No. 10 (May 15) 1990: pp. 2049-2052.

Donnelly et al., "Differential Regulation of II-1 Production in Human Monocytes by IFN-y and IL-4", The Journal of Immunology, vol. 145, 569-575. No. 2 Jul. 15, 1990.

Favier et al., Fecal B-D-Galactosidase Production and Bifidobacteria Are Decreased in Crohn's Disease, Digestive Diseases and Sciences, vol. 42, No. 4 (Apr. 1997), pp. 817-822.

Monteleone et al., "Manipulation of Cytokines in the Management of Patients With Inflammatory Bowel Disease", Ann Med. Nov. 2000:32(8):552-60.

Rogler et al., "Cytokines in Inflammatory Bowel Disease", World J Surg (1998) 22:382-9.

Strober et al., "Reciprocal IFN-gamma and TGF-Beta Responses Regulate the Occurrence of Mucosal Inflammation", Immunol Today. Feb. 1997;18(2):61-4.

Chadwick et al."Activation of the Mucosal Immune System in Irritable Bowel Syndrome", Gastroenterology (2002) 122:1778-83.

Anand et al."Cytokines and Inflammatory Bowel Disease", Tropical Gastroenterology. 1999; 20(3):97-106.

Gasche et al., "IL-10 Secretion and Sensitivity in Normal Human Intestine and inflammatory Bowel Disease", Journal of Clinical Immunology vol. 20, No. 5, 2000.

Hommes et al., "Anti- and Proinflammatory Cytokines in the Pathogenesis of Tissue Damage in Crohn's Disease", 2000 Lippincott Williams and Wilkins 1363-1950.

McKay et al., "Review article: In Vitro Models in Inflammatory Bowel Disease", Aliment Pharmacol Ther 1997: 11 (Suppl. 3): 70-80.

L. Lakatos, "Immunology of Inflammatory Bowel Diseases", Acta Physiologica Hungarica, vol. 87 (4), pp. 355-372 (2000).

Powrie et al., Inhibition of Th1 Responses Prevents Inflammatory Bowel Disease in Scid Mice Reconstituted with CD45Rbhi CD4+ T Cells, Immunity vol. 1, 553-562, Oct. 1994.

Van Damme et al., "The Proportion of Th1 Cells Which Prevail in Gut Mucosa, is Decreased in Inflammatory Bowel Syndrome", Clin Exp Immunol 2001: 125:383-390.

McBrearty, S., et al. "Probiotic Bifidobacteria and Their Identification Using Molecular Genetic Techniques," Teagasc, Dairy Products Research Centre, Moorepark, Fermoy, Co. Cork, Ireland, Department of Microbiology, University College Cork, Ireland, In J. Buttriss and M. Saltmarsh (ed), 2000, p. 97-107, Royal Scoeity of Chemistry, Cambridge, United Kingdom.

McCracken, V.J. et al., "Probiotics and the Immune System," in Probiotics: A Critical Review, Chapter Abstract, 1999.

O'Mahony, L., "Probiotic Bacteria and the Human Immune System," Proceedings of the British Nutrition Foundation / Royal Society of Chemistry (Food Chemistry Group) Symposium "Functional Foods '99—Claims and Evidence". BNF (London), 2000, p. 63-70.

O'Mahony, L., et al., "Probiotic Bacteria and Pathogenic Bacteria Elicit Differential Cytokine Responses From Dendritic Cells," Gatsroenterology, 120 (5) 1625 Suppl. Apr. 1, 2001.

Arai, K. et al., "Cytokines: Coordinators of Immune and Inflammatory Responses," Annu. Rev. Biochem., 1990, 59: 783-836.

Aranda, R., et al., "Analysis of Intestinal Lymphocytes in Mouse Colitis Mediated by Transfer of CD4+, CD45RB$^{high}$ T Cells to SCID Recipients,"1997, The Journal of Immunology, 158: 3464-3473.

Barbara. G. et al., "A Role for Inflammation In Irritable Bowel Syndrome?", GUT, Jul. 2002, 51: 141-144.

Brandwein, C., et al., "Genes, Bacteria, and T Cells: Ingredients for Inflammatory Bowel Disease," Selected Summaries, Gastroenterology. 1998, 115:1895-1600, J. Exp. Med 1998, 187:855-864.

Dunne, C., et al., "Probiotics: From Myth to Reality, Demonstration of Functionalitiy in Animal Models of Disease and in Human Clinical Trials," Antonie van Leewenhock, vol. 76, No. 1-4/pp. 279-292, Nov. 1999.

Hildesheim et al., "Simultaneous Measurement of Several Cytokines Using Small Volumes Of Biospecimens", *Cancer Epidemiology, Biomarkers & Prevention*, vol. IKI, pp. 1477-1484, Nov. 2002, XP002296946 abstract.

Andus et al., "Imbalance of the Interleukin 1 System in Colonic Mucosa—Association With Intestinal Inflammation and Interleukin 1 Receptor Agonist Genotype 2", *Gut*, vol. 41, 1997, pp. 651-657, p. 654, col. 2-p. 655, col. 1 figure 2D, XP002296947.

Rogler et al., "Cytokines in Inflammatory Bowel Disease", *World Journal of Surgery*, vol. 22, 1998, pp. 382-389, XP002296948 the whole document.

O'Callaghan et al., "Human Cytokine Production by Mesenteric Lymph Node Cells In Response To Probiotic and Pathogenic Bacteria", *Gastroenterology*, vol. 122, No. 4 Suppl. 1, p. A-151 DDW Meeting Abstract Nr. S1040, Apr. 2002, XP009036734 the whole document.

McCarthy et al., "Double Blind, Placebo Controlled Trial of Two Probiotic Straiins in Interleukin 10 Knockout Mice and Mechanistic Link With Cytokine Balance", *Gastroenterology.*, vol. 122, Nr. 4 Suppl. 1, pp. A-389-A390 DDW Meeting Abstract Nr. T962, XP009036733 the whole document, 2003.

Collins, J.K., "A Controlled Trial of Probiotic Treatment of IL-10 Knockout Mice," NUI, Cork, Cork, Ireland—AGA Abstracts, Gastroenterology, vol. 116, No. 4, Apr. 1999, G2981.

Collins, J.K., "Probiotics and Man—The Host Microbe Interface," NUI, Cork, Cork Ireland AGA Abstracts, Gastroenterology, vol. 116, No. 4, Apr. 1999, G2982.

Dunne. C., et al., "Epithelial Adhesion of Probiotic Microorganisms In Vitro and In Vivo," NUI, Cork Ireland, AGA Abstracts, Gastroenterology, vol. 116, No. 4, Apr. 1999, G3057.

O'Halloran, S., et al., "Adhesion of Potential Probiotic Bacteria to Human Epithelial Cell Lines," Departments of Microbiology and Medicine, University College, Mercy Hospita, Cork, Ireland, Department of Surgery, Mercy Hospita, Cork, Ireland, International Dairy J., 1998.

Scardovi, V., "Irregular Nonsporing Gram-Positive Rods," Irregular Nonsporing Gram-Positive Rods,J. Mol. Biol. 3, Section 15, pp. 1376-1379,, 1986.

\* cited by examiner

| | CORRELATION BETWEEN CHANGE IN IL-10 TO IL-12 RATIO AND CHANGE IN ABDOMINAL PAIN<br>CHANGE FROM BASELINE TO POST-TREATMENT MEASUREMENTS<br>AFTER TREATMENT WITH BIFIDOBACTERIUM | |
|---|---|---|
| STIMULUS | ABDOMINAL PAIN VAS SCORE | ABDOMINAL PAIN LIKER SCORE |
| NON-STIMULATED | -0.3457 (0.1150) | -0.3617 (0.0981) |
| BIFIDO 35624 | -0.2698 (0.2247) | -0.2699 (0.2244) |
| LACTO 4331 | -0.2938 (0.1845) | -0.2744 (0.2165) |
| AUTOLOGOUS FLORA | -0.5168 (0.0196) | -0.4959 (0.0262) |
| Pearson Correlation Coefficient ρ (p-value for testing ρ=0) | | |

Table 1.

METHODS OF DETERMINING EFFICACY OF TREATMENTS OF INFLAMMATORY DISEASES OF THE BOWEL

CROSS REFERENCE TO RELATED APPLICATION

This application is a continuation in part of U.S. application Ser. No. 10/404,512, filed Apr. 1, 2003.

TECHNICAL FIELD

The present invention relates to the field of inflammatory diseases of the bowel, particularly to methods for screening and determining efficacy of treatments of these diseases. Furthermore, kits to carry out the method of the present invention are also provided

BACKGROUND

Inflammatory diseases of the bowel is the general term for diseases that cause inflammation of the intestines such as irritable bowel syndrome (IBS), and the inflammatory bowel diseases (IBD) such as ulcerative colitis and Crohn's disease that are chronic inflammatory disorders of the gastrointestinal (GI) tract. For example, ulcerative colitis is an IBD that causes inflammation of the mucosa lining of the large intestine, usually occurring in the rectum and lower part of the colon, but it may affect the entire colon. Crohn's disease may affect any section of the GI tract (i.e. mouth, oesophagus, stomach, small intestine, large intestine, rectum and anus), and may involve all layers of the intestinal wall. The cause of many of these diseases is unknown.

IBS is a functional gastrointestinal disorder in which abdominal discomfort or pain is associated with defecation or change in bowel habit, and with features of disordered defecation. Theses symptoms represent a condition in which disturbances in motor and/or sensory function of the gut may be associated with psychosocial disorders, and the interaction leads to symptoms at several levels of the gastrointestinal tract.

IBS is now considered to be the most common gastrointestinal disorder. Prevalence in western world is estimated to be 15-20% of the adolescent and adult population and the disorder accounts for 20-50% of the referrals to gastroenterology clinics.

Current approaches to management of IBS consist of identification of symptoms consistent with the syndrome and the exclusion of organic disease with similar presentation, followed by non-pharmacological and pharmacological therapies, where appropriate. Current pharmacological therapeutic options are limited and the effectiveness of many is poorly documented. The current pharmacological therapies aim at treating symptoms with the rationale being either to modulate intestinal motility, decrease visceral sensitivity or treat associated disorders, particularly anxiety or depression.

The most common symptoms of IBD include abdominal pain, tenesmus, fecal urgency and bloody diarrhoea. Sufferers may also experience fatigue, weight loss, loss of appetite, rectal bleeding and loss of body fluids and electrolytes. The symptoms of the disease are usually progressive, and sufferers typically experience periods of remission followed by severe flare-ups.

Despite the prevalence of IBD (it affects an estimated 2 million people in the United States alone), there is no cure and the exact causes of the disease are not yet understood. Conventional treatments for IBD have involved anti-inflammatory drugs, immunosuppressive drugs and surgery. However, many of the drugs used for treating the disease have negative side effects such as nausea, dizziness, anaemia, leukopaenia, skin rashes and drug dependence, and the surgical procedures are often radical procedures, such as intestinal resectomy and colectomy.

This has led to several investigators to attempt to identify new and novel drugs for treatment of the inflammatory diseases of the bowel. Unfortunately, the very nature of the disease means that screening and measuring the efficacy of potential treatments in human subjects is very difficult. Often, the results of human trials depend upon subjective testimony from the trial candidates themselves, with little or no biochemical or physiological data to substantiate claims. Animal models may be used to allow tissue sections from affected organs to be taken, but drugs effective in animal models do not always have the same efficacy in humans.

The control of inflammatory diseases is exerted at a number of levels. The controlling factors include hormones, prostaglandins, reactive oxygen and nitrogen intermediates, leukotrienes and cytokines. Cytokines are low molecular weight biologically active proteins that are involved in the generation and control of immunological and inflammatory responses. A number of cell types produce these cytokines, with neutrophils, monocytes and lymphocytes being the major sources during inflammatory reactions due to their large numbers at the injured site.

Multiple mechanisms exist by which cytokines generated at inflammatory sites influence the inflammatory response. Chemotaxis stimulates homing of inflammatory cells to the injured site, whilst certain cytokines promote infiltration of cells into tissue. Cytokines released within the injured tissue result in activation of the inflammatory infiltrate. Most cytokines are pleiotropic and express multiple biologically overlapping activities. Cytokine cascades and networks control the inflammatory response, rather than the action of a particular cytokine on a particular cell type. As uncontrolled inflammatory responses can result in diseases such as inflammatory diseases of the bowel, it is reasonable to expect that cytokine production has gone astray in individuals affected with these diseases. However, as many cytokines may have both pro- and anti-inflammatory activities, it is very difficult to attribute disease symptoms, or recovery there from, with a particular individual cytokine.

Based on the forgoing, it is desirable to provide methods for screening and measuring the efficacy of potential treatments for inflammatory diseases of the bowel in humans or other mammals that generate biochemical or physiological data. This data could be used to evaluate the efficacy of the treatment. It is further desirable to provide methods for measuring changes in the levels of specific cytokines potentially involved in the pathogenesis of inflammatory diseases of the bowel such that the prognosis and disease progression of a subject with inflammatory diseases of the bowel can be monitored.

SUMMARY

The present invention provides novel methods for determining the efficacy of a treatment of inflammatory diseases of the bowel in mammals in vivo comprising the steps of:
a) measuring the level of at least one anti-inflammatory cytokine and at least one pro-inflammatory cytokine in a biological sample from a mammalian subject;
b) determining the ratio of the at least one anti-inflammatory cytokine to the at least one pro-inflammatory cytokine;

c) administering said treatment;
d) measuring the level of the at least one anti-inflammatory cytokine and the at least one pro-inflammatory cytokine in a biological sample from said mammalian subject at a time following administration of said treatment;
e) determining the ratio of the at least one anti-inflammatory cytokine to the at least one pro-inflammatory cytokine following administration of said treatment;

wherein, an increase in the ratio of anti-inflammatory cytokine to pro-inflammatory cytokine following the administration of said treatment is indicative of an inhibitor of inflammatory diseases of the bowel, and no change or a decrease in the ratio of anti-inflammatory cytokine to pro-inflammatory cytokine following the administration of said treatment is indicative of said treatment not being an inhibitor of inflammatory diseases of the bowel.

In addition, the present invention provides in vitro methods for screening compositions for efficacy in the treatment of inflammatory diseases of the bowel comprising the steps of:
a) providing a biological sample comprising at least one gut-derived cell type;
b) treating said biological sample with the composition in vitro;
c) measuring the level of at least one anti-inflammatory cytokine and at least one pro-inflammatory cytokine in the biological sample at a time following treatment with the composition;
d) determining the ratio of the at least one anti-inflammatory cytokine to the at least one pro-inflammatory cytokine in the biological sample at a time following treatment with the composition;

characterised in that a ratio as determined in step (d) from the treated biological sample greater than the same ratio determined in an untreated control biological sample tested concurrently is indicative of the composition being an inhibitor of inflammatory diseases of the bowel, and a ratio as determined in (d) the same as or less than the untreated control biological sample ratio is indicative of the composition not being an inhibitor of inflammatory diseases of the bowel.

The present invention is also directed towards providing further use of the methods herein, and kits for carrying out the methods herein.

Table 1 demonstrates the Pearson's correlation coefficients and p-values for testing the statistical significance of the negative association between the change in IL-10 to IL-12 ratio and the change in abdominal pain/discomfort score in IBS patients fed with *Bifidobacterium infantis*. Note that the mean IL-10 to IL-12 ratio increased and the mean abdominal pain/discomfort score decreased from pre- to post-feeding with *Bifidobacterium infantis*.

Figure 4:
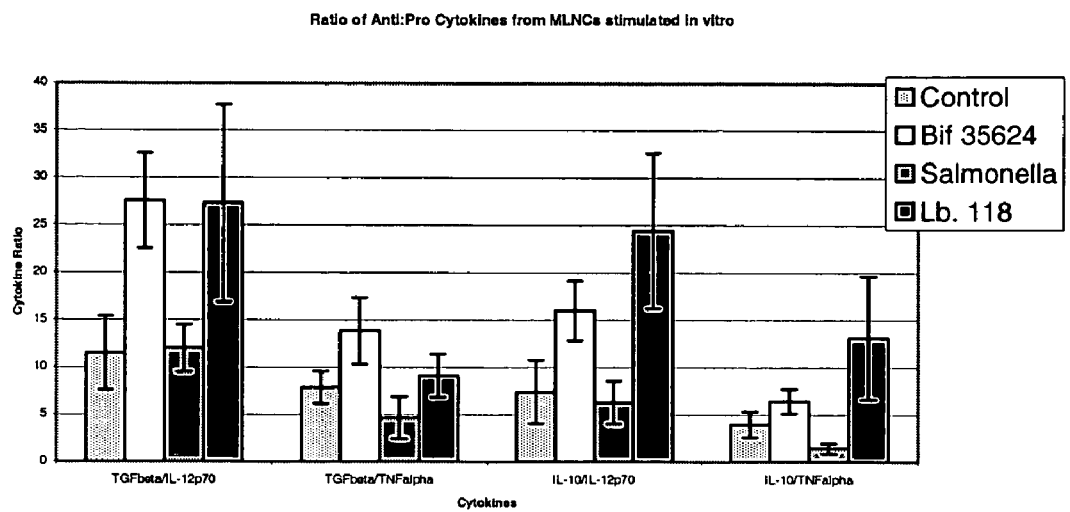

FIG. 4 is a bar graph that demonstrates the ratio of anti-inflammatory cytokines to pro-inflammatory cytokines produced by mesenteric lymph node cells (MLNCs) stimulated in vitro.

Figure 5:
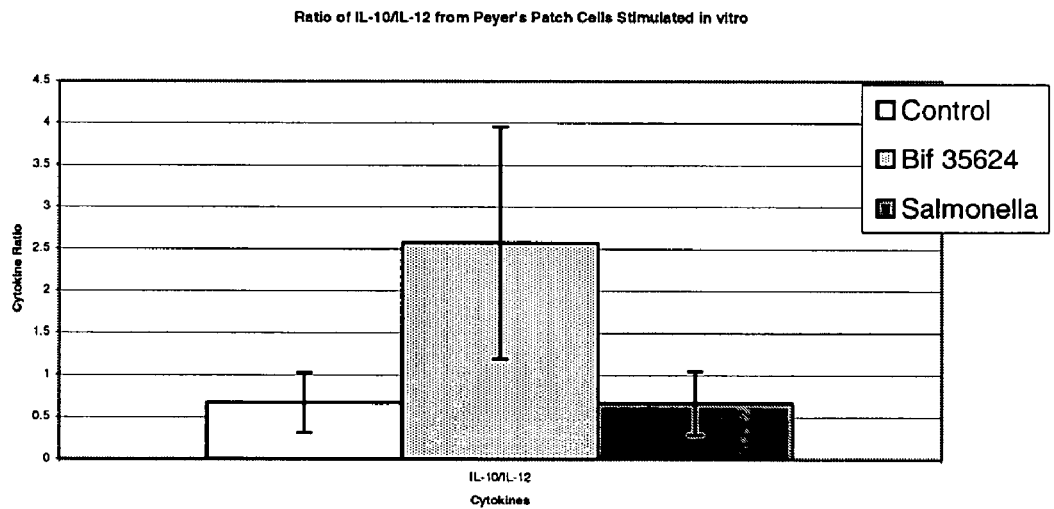

FIG. 5 is a bar graph that demonstrates the ratio of anti-inflammatory cytokines to pro-inflammatory cytokines produced by Peyer's patch cells (PPs) stimulated in vitro.

Figure 6:
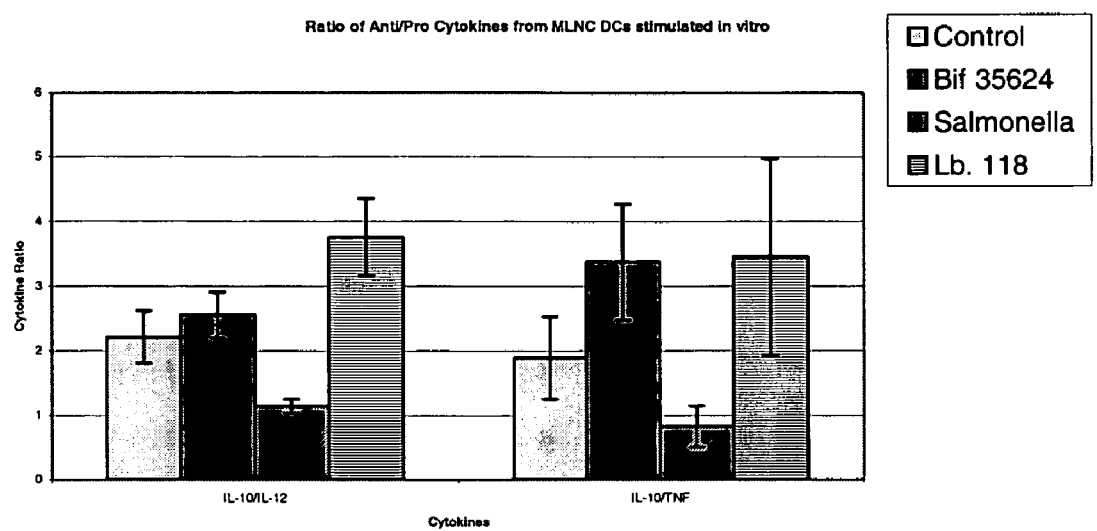

FIG. 6 is a bar graph that demonstrates the ratio of anti-inflammatory cytokines to pro-inflammatory cytokines produced by mesenteric lymph node cell-derived dendritic cells (MLNC DCs) stimulated in vitro.

DETAILED DESCRIPTION OF THE INVENTION

All weights, measurements and concentrations herein are measured at 25° C. on the composition in its entirety, unless otherwise specified.

Unless otherwise indicated, all percentages of compositions referred to herein are weight percentages and all ratios are weight ratios.

Unless otherwise indicated, all molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

As used herein, "inflammatory diseases of the bowel" include "irritable bowel syndrome—IBS" and "inflammatory bowel disease—IBD".

As used herein, "inflammatory bowel disease" or "IBD" includes diseases that cause inflammation of the intestines such as ulcerative colitis and Crohn's disease.

Methods and Use

The present invention is directed towards providing methods of determining efficacy of a treatment of inflammatory diseases of the bowel in vivo in mammals comprising the steps of:
a) measuring the level of at least one anti-inflammatory cytokine and at least one pro-inflammatory cytokine in a biological sample from a mammalian subject;
b) determining the ratio of the at least one anti-inflammatory cytokine to the at least one pro-inflammatory cytokine;
c) administering said treatment;
d) measuring the level of the at least one anti-inflammatory cytokine and the at least one pro-inflammatory cytokine in a biological sample from said mammalian subject at a time following administration of said treatment;
e) determining the ratio of the at least one anti-inflammatory cytokine to the at least one pro-inflammatory cytokine following administration of said treatment;

wherein, an increase in the ratio of anti-inflammatory cytokine to pro-inflammatory cytokine following the administration of said treatment is indicative of an inhibitor of inflammatory diseases of the bowel, and no change or a decrease in the ratio of anti-inflammatory cytokine to pro-inflammatory cytokine following the administration of said treatment is indicative said treatment not being an inhibitor of inflammatory diseases of the bowel. The method of the present invention comprises measuring and determining the ratio of at least one anti-inflammatory cytokine and at least one pro-inflammatory cytokine before the treatment is administered. This may include determining the levels and ratios therein at least once before treatment is commenced, ideally at day 0, immediately before the treatment is commenced. Alternatively, the levels and ratio of said cytokines may be determined repeatedly over a given time before the commencement of treatment in order to provide a baseline measurement as known to those skilled in the art. The method of the present invention may further comprise repeating steps (d) and (e) at least once at similar time points following the administration of said treatment. Furthermore, the method of the present invention may comprise repeating steps (d) and (e) at least once at similar time points whilst said mammalian subject is still being administered said treatment. The method of the present invention may be utilised to both screen and clinically evaluate unknown or new treatments or compositions for efficacy in the treatment of inflammatory diseases of the bowel. Furthermore, the method of the present invention may also be used to monitor the efficacy of a known treatment in an individual patient with inflammatory disease of the bowel. Further still, the method herein may be used to provide a predictive biomarker for inflammatory diseases of the bowel helpful in diagnosis of the disorder.

In addition, the present invention provides in vitro methods for screening compositions for efficacy in the treatment of inflammatory diseases of the bowel comprising the steps of:
  a) providing a biological sample comprising at least one gut-derived cell type;
  b) treating said biological sample with the composition in vitro;
  c) measuring the level of at least one anti-inflammatory cytokine and at least one pro-inflammatory cytokine in the biological sample at a time following treatment with the composition;
  d) determining the ratio of the at least one anti-inflammatory cytokine to the at least one pro-inflammatory cytokine in the biological sample at a time following treatment with the composition;
characterised in that a ratio as determined in step (d) from the treated biological sample greater than the same ratio determined in an untreated control biological sample tested concurrently is indicative of the composition being an inhibitor of inflammatory diseases of the bowel, and a ratio as determined in (d) is the same as or less than the untreated control biological sample ratio is indicative of the composition not being an inhibitor of inflammatory diseases of the bowel.

The methods herein are suitable for use in screening and determining clinical efficacy of treatments and compositions for the treatment of inflammatory diseases of the bowel. These diseases include inflammatory gastro-intestinal disorders, some non-limiting examples of which include irritable bowel syndrome (IBS), and IBDs such as ulcerative colitis and Crohn's disease. Preferably, the method herein is used to determine the efficacy of treatments for irritable bowel syndrome (IBS).

The treatments herein include any treatment and/or composition for use in the treatment of inflammatory diseases of the bowel. The compositions may comprise one or more ingredients that are to have their potential efficacy in the treatment of inflammatory diseases of the bowel, preferably IBS, determined. Non-limiting examples of such compositions include anti-inflammatory drugs, probiotic compositions, new compositions and compounds not known to have efficacy in the treatment of inflammatory diseases of the bowel, compositions and compounds known to alleviate the symptoms of inflammatory diseases of the bowel including new delivery forms of known drugs useful in the treatment of inflammatory diseases of the bowel and mixtures thereof.

The in vivo methods of the present invention are also of use in determining the response of an individual sufferer of inflammatory diseases of the bowel to a composition useful in the treatment of inflammatory disease of the bowel. This allows the determination of the efficacy of a given treatment in an individual sufferer of inflammatory disease of the bowel, and enables physicians to monitor the progress of patients, and to determine whether to change drug type or delivery form in order to optimise the treatment of the patient. This would result in the patient receiving better treatment for their disease, and a decrease in the amount of drugs and money wasted on treatments that are ineffective on a population of sufferers of inflammatory diseases of the bowel.

Biological Sample for the In Vivo Method

The method of the present invention comprises measuring cytokine levels in a biological sample obtained from a mammalian subject both before and during or after administration of said treatment. Non-limiting examples of mammalian subjects suitable for use herein include human, simian, canine, feline, bovine, ovine, porcine, rodent subjects including murine and rat species, rabbit or equine subjects, preferably a human subject. Biological samples useful herein will be well-known to one skilled in the art. As used herein, "biological sample" includes urine, plasma, serum, saliva, tissue biopsies, cerebrospinal fluid, peripheral blood mononuclear cells with in vitro stimulation, peripheral blood mononuclear cells without in vitro stimulation, gut lymphoid tissues with in vitro stimulation, gut lymphoid tissues without in vitro stimulation, gut lavage fluids, and mixtures thereof. Preferably, the biological sample used in the in vivo method of the present invention comprises serum, tissue biopsies, peripheral blood mononuclear cells with in vitro stimulation, peripheral blood mononuclear cells without in vitro stimulation, and mixtures thereof, more preferably peripheral blood mononuclear cells with in vitro stimulation, peripheral blood mononuclear cells without in vitro stimulation, and mixtures thereof. Peripheral blood mononuclear cells (PBMC) may be harvested from EDTA-treated, non-coagulated venous blood using methods known to those skilled in the art, such as Ficoll-Hypaque density centrifugation. More preferably still, the in vivo method of the present invention utilizes a biological sample comprising peripheral blood mononuclear cells with in vitro stimulation. As used herein, "peripheral blood mononuclear cells" with or without in vitro stimulation includes freshly harvested PBMC, whole cell homogenates of freshly harvested PBMC, extracted protein fractions of freshly harvested PBMC, mRNA transcripts from freshly harvested PBMC, tissue culture medium supernatants of freshly harvested PBMC, frozen PBMC, whole cell homogenates of frozen PBMC, extracted protein fractions of frozen PBMC, mRNA transcripts from frozen PBMC, tissue culture medium supernatants of frozen PBMC, in vitro cultures of harvested PBMC, whole cell homogenates of in vitro cultures of harvested PBMC, extracted protein fractions of in vitro cultures of harvested PBMC, mRNA transcripts from in vitro cultures of harvested PBMC, tissue culture medium supernatants of in vitro cultures of harvested PBMC, and mixtures thereof.

As used herein "in vitro stimulation" includes the stimulation of biological samples outside of the donor's body, typically in a laboratory tissue culture setting. Preferably, the stimulus comprises a mitogen, probiotic, anti-CD3 molecules known to those skilled in the art, and mixtures thereof. More preferably, the stimulus comprises a mitogen, probiofic, and mixtures thereof.

As used herein, "mitogen" includes materials that are capable of inducing cell division in a high percentage of T or B cells. Suitable of examples of mitogens useful herein include lectins, bacterial lipopolysaccharides, super-antigens and mixtures thereof. As used herein, "super-antigen" includes materials that can bind to residues in the V (variable)

domain of the T-cell receptor and to residues in class II MHC molecules outside of the antigen-binding cleft, even when the T-cell receptor does not recognise the antigenic peptide bound to the class II MHC molecule. Suitable examples of super-antigens useful herein include staphylococcal enterotoxins, toxic shock syndrome toxin 1, and mixtures thereof. Preferably, the mitogen comprises lectins, bacterial lipopolysaccharides, and mixtures thereof. Suitable examples of lectins useful herein include concanavalin A (isolated from Jack beans), phytohemagglutinin (isolated from kidney beans), pokeweed mitogen (isolated from pokeweed) and mixtures thereof, preferably phytohemagglutinin (PHA). Suitable examples of bacterial lipopolysaccharides useful herein include *Escherichia coli* (*E. coli*) 0111:B4, *E. coli* 055:B5, *E. coli* K-235 (all available from Sigma (St Louis, Mo.)), *Salmonella Minnesota, Salmonella typhimurium, Shigella flexneri, Klebisella pneumonia, Pseudomonas aeruginosa*, and mixtures thereof.

Probiotics are micro-organisms, or processed compositions of micro-organisms which beneficially affect a host. How probiotics beneficially affect the host is unknown. For the purpose of the present invention, "probiotics" is further intended to include the metabolites generated by the micro-organism during a fermentation process, if they are not separately indicated. These metabolites may be released to the medium of fermentation, or they may be stored within the micro-organism. As used herein "probiotic" also includes bacteria, bacterial homogenates, bacterial proteins, bacterial extracts, bacterial supernatants, and mixtures thereof, that perform beneficial functions for the host when given at a therapeutic dose. Therefore, yeasts, moulds and bacteria may be included. EP 0862863 lists some examples of probiotics presently known. Suitable examples of probiotics useful herein comprise strains of *Bifidiobacterium longum infantis* (NCIMB 35624) *Lactobacillus johnsonii* (CNCM I-1225), *Bifidobacterium lactis* (DSM20215), *Lactobacillus paracasei* (CNCM I-2216), and mixtures thereof. Further non-limiting examples of probiotics useful herein are described in WO 03/010297 A1, WO 03/010298 A1, WO 03/010299 A1 (all published Feb. 6, 2003 and assigned to Alimentary Health Ltd).

Biological Sample for the In Vitro Method

The in vitro method of the present invention utilises a biological sample comprising at least one gut-derived cell type. Use of the gut-derived cell type in the in vitro method has been found to be advantageous over prior art in vitro methods involving other tissues such as, for example, peripheral blood mononucleocytes. Without being bound by theory, this is though to be because the interaction between the composition for treating inflammatory diseases of the bowel to be screened and the gut is more indicative of what is occurring in vivo. It has been found that the in vitro screening method herein more readily identifies potential treatments of inflammatory diseases of the bowel, and has an improved correlation with clinical efficacy. Without being bound by theory, this is thought to be due to the fact that in inflammatory diseases of the bowel, it is the gut tissue that plays a central role in mediating the inflammatory response, and therefore those compositions that beneficially alter the cytokine ratio of gut-derived cell types in vitro are more likely to have an effect in vivo.

As used herein "gut-derived cell type" includes cell types and strains that have their origin in a mammalian gut or gut-associated tissue, said tissue including the stomach, duodenum, jejunum, ileum, lymphoid, mesentery, axillary, inguinal, popliteal, myeloid, cecum, colon, appendix and rectum. Furthermore, such cell types also include cells freshly isolated from said tissues, and cell types that have been routinely cultured in vitro following isolation from the above tissues, including non-immortalized cell lines, carcinogenic and otherwise immortalized cell lines. Preferably, the in vitro method utilises a biological sample comprising gut-associated lymphoid tissues, either freshly isolated, or in vitro cell cultures thereof. More preferably, the biological sample comprises mesenteric lymph node cells, either freshly isolated, or in vitro cell cultures thereof.

Furthermore, the in vitro method of the present invention may additionally comprise the further step of stimulating the biological sample prior to step (c) above. As used herein "in vitro stimulation" includes the stimulation of biological samples outside of the donor's body, typically in a laboratory tissue culture setting. Preferably, the stimulus comprises a mitogen, probiotic, anti-CD3 molecules known to those skilled in the art, and mixtures thereof. More preferably, the stimulus comprises a mitogen, probiotic, and mixtures thereof.

As used herein, "mitogen" includes materials that are capable of inducing cell division in a high percentage of T or B cells. Suitable of examples of mitogens useful herein include lectins, bacterial lipopolysaccharides, super-antigens and mixtures thereof. As used herein, "super-antigen" includes materials that can bind to residues in the V (variable) domain of the T-cell receptor and to residues in class II MHC molecules outside of the antigen-binding cleft, even when the T-cell receptor does not recognise the antigenic peptide bound to the class II MHC molecule. Suitable examples of super-antigens useful herein include staphylococcal enterotoxins, toxic shock syndrome toxin 1, and mixtures thereof. Preferably, the mitogen comprises lectins, bacterial lipopolysaccharides, and mixtures thereof. Suitable examples of lectins useful herein include concanavalin A (isolated from Jack beans), phytohemagglutinin (isolated from kidney beans), pokeweed mitogen (isolated from pokeweed) and mixtures thereof, preferably phytohemagglutinin (PHA). Suitable examples of bacterial lipopolysaccharides useful herein include *Escherichia coli* (*E. coli*) 0111:B4, *E. coli* 055:B5, *E. coli* K-235 (all available from Sigma (St Louis, Mo.)), *Salmonella Minnesota, Salmonella typhimurium, Shigella flexneri, Klebisella pneumonia, Pseudomonas aeruginosa*, and mixtures thereof.

Probiotics are micro-organisms, or processed compositions of micro-organisms which beneficially affect a host. How probiotics beneficially affect the host is unknown. For the purpose of the present invention, "probiotics" is further intended to include the metabolites generated by the micro-organism during a fermentation process, if they are not separately indicated. These metabolites may be released to the medium of fermentation, or they may be stored within the micro-organism. As used herein "probiotic" also includes bacteria, bacterial homogenates, bacterial proteins, bacterial extracts, bacterial supernatants, and mixtures thereof, that perform beneficial functions for the host when given at a therapeutic dose. Therefore, yeasts, moulds and bacteria may be included. EP 0862863 lists some examples of probiotics presently known. Suitable examples of probiotics useful herein comprise strains of *Bifidiobacterium longum infantis* (NCIMB 35624) *Lactobacillus johnsonii* (CNCM I-1225), *Bifidobacterium lactis* (DSM20215), *Lactobacillus paracasei* (CNCM I-2216), and mixtures thereof. Further non-limiting examples of probiotics useful herein are described in WO 03/010297 A1, WO 03/010298 A1, WO 03/010299 A1 (all published Feb. 6, 2003 and assigned to Alimentary Health Ltd).

Cytokines

The methods of the present invention comprise the step of measuring at least one anti-inflammatory and at least one pro-inflammatory cytokine levels in a biological sample obtained from a mammalian subject. In the in vivo method, said samples are collected both before and after treatment with the composition of interest. It is known to those skilled in the art that cytokines are pleiotropic, and express multiple biologically overlapping activities. Accordingly, it should be understood that although the cytokines useful herein are categorized by their inflammatory action in the present system, some such ingredients can in some instances provide more than one immune response action. Therefore, the classifications herein are made for the sake of convenience.

Anti-inflammatory cytokines useful in the present invention comprise those known in the art. Non-limiting examples of anti-inflammatory cytokines useful herein include interleukin-4, interleukin-5, interleukin-13 interleukin-10, transforming growth factor-□, and mixtures thereof. Preferred anti-inflammatory cytokines for use in the present invention include interleukin-10 (IL-10: accession number: CAA55201; GI accession ID: 14625940), transforming growth factor-β isoforms 1, 2, 3 and 4, and mixtures thereof. Pro-inflammatory cytokines useful in the present invention comprise those known in the art. Non-limiting examples of pro-inflammatory cytokines useful herein include interleukin-2, heterodimeric interleukin-12, tumour necrosis factor-α, tumour necrosis factor-□, interferon-γ, and mixtures thereof. Preferred pro-inflammatory cytokines useful herein include heterodimeric interleukin-12 (IL-12: accession number: chain A; 1F45A, chain B; 1F45B; GI accession ID: chain A; 1479640; chain B; 1479641), tumour necrosis factor-α (TNF: accession number: AAC03542; GI accession ID: 2905634), interferon-γ (INF: accession number: NP_000610; GI accession ID: 10835171), and mixtures thereof.

Means for Measuring Levels

According to the method of the present invention, the levels of at least one anti-inflammatory cytokine and at least one pro-inflammatory cytokine in the biological sample are measured. Means for measuring the levels of anti-inflammatory or pro-inflammatory cytokines, or both, comprise methods known to those skilled in the art. The levels of said anti-inflammatory and said pro-inflammatory cytokines may be measured by measuring mRNA expression or protein expression, as is known to one skilled in the art. Non-limiting examples of such methods include immunosorbent assays, enzyme-linked immunosorbent assays (ELISAs), radioimmunoassays (RIAs), multiplexed ELISAs on microarray platforms, multiplexed ELISAs using coded microspheres coupled with a flow cytometer detection systems, bioassays, Western blots, chromatograph-based separation systems, RT-PCR, competitive reverse transcription PCR, Northern blots, gene arrays, direct measurement of m-RNA, and mixtures thereof, preferably ELISAs, RIAs, multiplexed ELISAs using coded microspheres coupled with a flow cytometer detection systems, chromatograph-based separation systems, western blots, and mixtures thereof. More preferably the means comprises multiplexed ELISAs using coded microspheres coupled with a flow cytometer detection systems. Suitable ELISAs for use in the method of the present invention comprise those known to those skilled in the art, non-limiting examples of which include direct ELISAs, indirect ELISAs, direct sandwich ELISAs, indirect sandwich ELISAs, and mixtures thereof. A non-limiting example of commercially available multiplexed ELISAs using coded microspheres coupled with a flow cytometer detection systems suitable for use herein is the LINCOplex kit assay available from Linco Research Inc., Mo., USA coupled with a BIOPLEX BEAD FLOW CYTOMETER™ from Bio Rad GmbH.

Ratio

The methods of the present invention comprise the steps of determining the ratio of at least one anti-inflammatory cytokine to at least one pro-inflammatory cytokine. In the in vivo method, these levels are determined both before administration of the treatment, and determining the same ratio either during the treatment or following completion of the treatment. In the in vitro method, the levels of at least one anti-inflammatory cytokine to at least one pro-inflammatory cytokine are determined in the treatment sample, and an untreated control biological sample tested concurrently. The control biological sample must be derived from the same biological sample as that used for the treatment group, and must be run as an untreated control using methods and principles known to those skilled in the art. As used herein, the ratio of anti-inflammatory cytokine to pro-inflammatory cytokine means the level of anti-inflammatory cytokine divided by the level of pro-inflammatory cytokine. Such ratio can be described by the formula:

Ratio=Level of Anti-Inflammatory Cytokine Level of Pro-Inflammatory Cytokine

Without wishing to be bound by theory, it is believed that according to the present invention, if the ratio as determined herein increases after or during treatment, when compared with the ratio determined prior to the commencement of treatment or the untreated control biological sample, then the treatment is considered to be an inhibitor of inflammatory diseases of the bowel. The ratio herein can be determined using any anti-inflammatory cytokine, and any pro-inflammatory cytokine herein. Preferably, the ratios useful herein include the ratio IL-10/IL-12, the ratio IL-10/IFN-□, the ratio of □L₁/TNF-□, and mixtures thereof. Without wishing to be bound by theory, it is believed that the specific ratios described herein are pivotal to the progression or remission of inflammatory diseases of the bowel, and therefore alterations in the ratios herein are indicative of the inhibition or promotion of disease effects by treatments being investigated. It appears that individuals with inflammatory diseases of the bowel have a skewed cytokine profile that is indicative of an inflammatory condition. Similarly, the cytokines used herein that demonstrate the greatest change following treatment with inhibitors of inflammatory diseases of the bowel indicate that sufferers of these diseases have PBMC that are biased towards greater Th-1 activity, altering the normal Th-1/Th-2 cytokine balance. It has surprisingly been found that by increasing the ratios described herein, the symptoms of inflammatory diseases of the bowel can be alleviated. Without wishing to be bound by theory, it is believed that this is due to the fact that by increasing these ratios in sufferers of inflammatory diseases of the bowel, the treatment brings the ratios back up towards, or close to, those levels found in healthy subjects.

Kits

According to the present invention, kits are provided for carrying out the method of the present invention. Preferably the kits comprise a first measuring element or system for measuring at least one anti-inflammatory cytokine in a biological sample from a mammalian subject before treatment and at at least one time point after or during treatment, a second measuring element or system for measuring at least one pro-inflammatory cytokine in a biological sample from said mammalian subject before treatment, and at at least one time point after or during treatment, wherein the change in ratio of anti-inflammatory to pro-inflammatory cytokine after administration of the treatment can be determined. Such measuring elements or systems may include those known to one skilled in art, non-limiting examples of which include immunosorbent assays, enzyme-linked immunosorbent assays (ELISAs), radioimmunoassays (RIAs), multiplexed ELISAs on microarray platforms, multiplexed ELISAs using coded microspheres coupled with a flow cytometer detection systems, bioassays, Western blots, chromatograph-based separation systems, RT-PCR, competitive reverse transcription PCR, Northern blots, gene arrays, direct measurement of m-RNA, and mixtures thereof, preferably ELISAs, RIAs, multiplexed ELISAs using coded microspheres coupled with a flow cytometer detection systems, chromatograph-based separation systems, western blots, and mixtures thereof, more preferably multiplexed ELISAs using coded microspheres coupled with a flow cytometer detection systems. The kits of the present invention may further comprise means for obtaining the biological sample from the subject. Such means may comprise venous blood collection tubes and devices for collecting said blood, sample tubes for urine or saliva, means for separating PBMCs from venous blood, and mixtures thereof.

Furthermore, the kits of the present invention may comprise instructions for use. The instructions for use may comprise language indicating how to determine the ratio according to the present invention, and/or language indicating what the results of the performed method mean. A non-limiting example of such instructions includes language indicating that an increase in the ratio of anti-inflammatory cytokine to pro-inflammatory cytokine is indicative of an inhibitor of inflammatory diseases of the bowel.

EXAMPLES

In Vivo Methodology

Ten healthy adults and 13 self-reported irritable bowel syndrome (IBS) patients were fed daily with probiotic preparation of 100 ml milk containing $10^8$ colony forming units (CFUs)/ml of *Bifidobacterium infantis* 35624 (a potential treatment of IBS) for 3 weeks. Venous blood was drawn from each subject before and after oral feeding with the probiotic preparation. Venous blood was collected into blood collection tubes (CPT™ VACUTAINER cell separation tubes containing sodium heparin, Becton Dickinson, Franklin Lakes, N.J.). PBMC were isolated from the blood using by centrifugation at 400×g, and subsequently cultured in vitro in appropriate cell culture conditions as known to one skilled in the art. Dulbecco's Minimum Essential Media (DMEM) supplemented with 100 U/ml penicillin G/100 □g/ml streptomycin (Gibco), 2.5 □g/ml fungizone (Gibco), 292 □g/ml L-glutamine (Gibco) and 10% foetal calf serum (#1103155, Gibco) was used herein for all cell cultures except for the measurement of TGF-□ wherein the foetal calf serum was left out. The isolated PBMC suspension was adjusted to a viable cell count of $1.3\times10^6$/ml and were cultured either alone in medium (no stimulation), or with 0.1 □g/ml *E. coli* 0111B4 lipopolysaccharide (Sigma, St Louis, Mo.), 1 □g/ml phytohemagglutinin (PHA—Sigma, St Louis, Mo.) or $10^7$ CFU/ml whole *Bifidobacterium infantis* 35624 for 3 days. Subsequently, cell suspensions were collected into microfuge tubes and centrifuged in an MRX-152 microfuge (Tomy Tech, Palo Alto, Calif.) at 10 000 rpm at 4° C. for 3 minutes and supernatants collected for analysis.

The quantity of cytokines in supernatants were analysed by using the commercially available LINCOplex kit assay (from Linco Research Inc., Mo., US) in a BIOPLEX BEAD FLOW CYTOMETER™ (Bio Rad, Hercules, Calif.). Twenty-five □l of culture supernatant were incubated with a panel of microsphere beads coated with antibodies specific to the cytokines interleukin-10 (IL-10), interleukin-12 (IL-12), tumour necrosis factor-α (TNF), interferon-γ (INF), and transforming growth factor-β (TGF) (LINCOplex kit assay from Linco Research Inc., Mo., US). Bead mixtures were washed and further incubated with streptavidin-phycoerythrin at room temperature for 30 minutes. Concurrently, controls and standards, prepared in serial dilutions were also incubated with the aforementioned procedures. Bead suspensions were washed and resuspended in buffer for reading by the BIOPLEX system. The cytokine levels were quantitated in units of pg/ml. The cytokine levels in both populations and the feeding effects were analysed statistically with Student's paired t-test.

Figure 1:
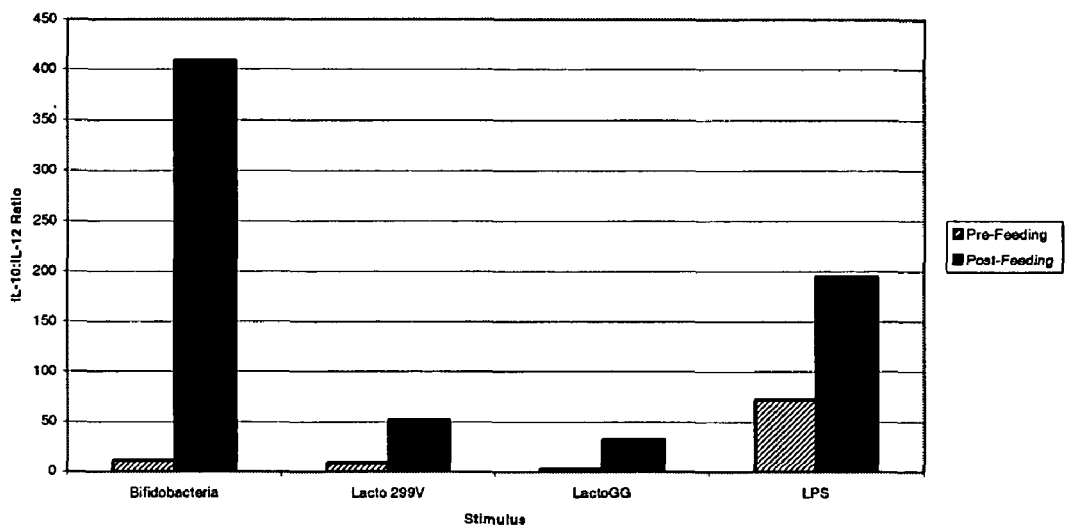
FIG. 1 is a bar graph demonstrating the mean ratio of IL-10 to IL-12 generated from PBMCs from IBS patients with in vitro stimulation both pre- and post-feeding with *Bifidobacteria infantis*.

Daily oral feeding with probiotic *Bifidobacterium infantis* 35624 for 3 weeks increased the ratio IL-10/IL-12 from 11.2±3.9 (mean±standard error) to 409.5±95.2 in IBS patients' PBMC with in vitro stimulation by *Bifidobacterium infantis* 35624. Similarly, when PBMC from the IBS population were stimulated in vitro with other probiotics including *Lactobacillus* 299V and *Lactobacillus* GG, similar increases in the IL-10/IL-12 ratio were observed (see FIG. 1).

Figure 2:
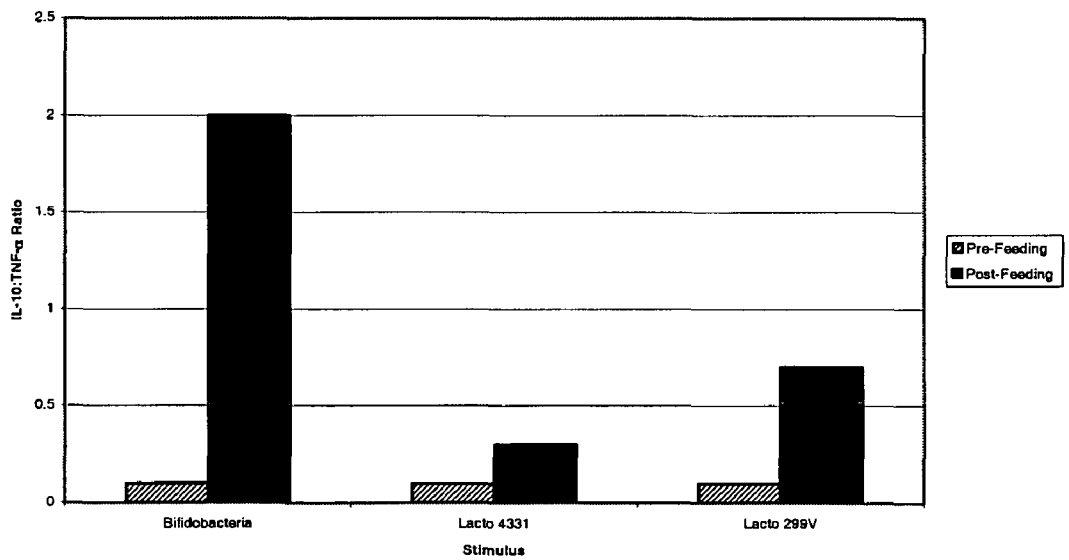
FIG. 2 is a bar graph demonstrating the mean ratio of IL-10 to TNF-☐ generated from PBMCs from IBS patients with in vitro stimulation both pre- and post-feeding with *Bifidobacteria infantis*.
Figure 3:
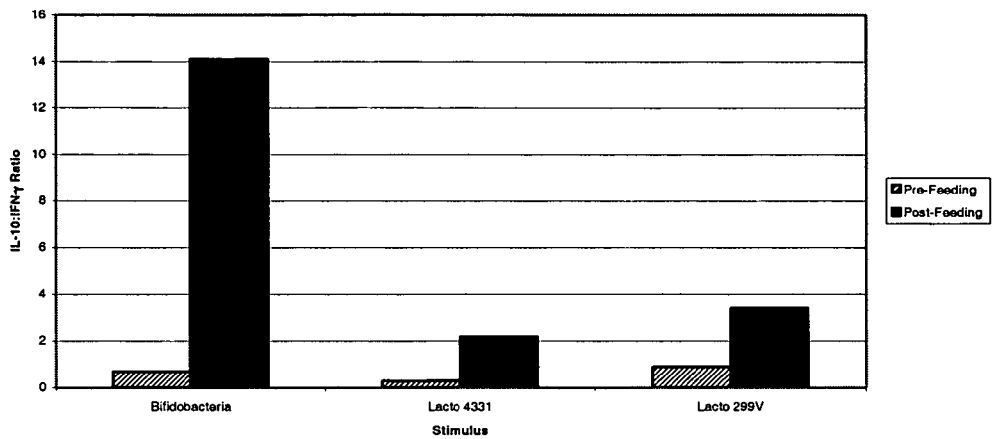
FIG. 3 is a bar graph demonstrating the mean ratio of IL-10 to IFN-☐ generated from PBMCs from IBS patients with in vitro stimulation both pre- and post-feeding with *Bifidobacteria infantis*.

Additionally, probiotic stimulation (*Bifidobaterium*) of PBMC from IBS patients after feeding demonstrated an increase from 0.1±0.0 to 2.0±0.5 in the ratio IL-10/TNF-□□ similar results were also seen following stimulation with other probiotics including *Lactobacillus* 4331 and *Lactobacillus* 299V (see FIG. 2). Also, stimulation with probiotic *Bifidobacterium infantis* 35624 resulted in an increase in the IL-10/IFN-□ ratio from 0.7±0.1 to 14.1±2.3 following treatment (see FIG. 3).

Furthermore, it was observed that the mean abdominal pain/discomfort decreased and the mean IL-10 to IL-12 ratio increased in those IBS patients treated with *Bifidobacterium infantis*. The negative correlation between the change in abdominal pain/discomfort and the change in IL-10 to IL-12 ratio indicatedthat the increase in IL-10 to IL-12 ratio was associated with the relief from IBS symptom of abdominal pain/discomfort (see Table 1).

In Vitro Methodology

This study was approved by the Ethics Committee of Cork University Hospital. Mesenteric lymph nodes were obtained from ten patients with active IBD (n=10: age range 19-41 (mean 32.2), 3 women and 7 men: 5 patients with CD; 5 patients with UC). All patients were prescribed and taking 5'-amino salicylic acid. All patients required surgical section because of progressive disease and failure to respond to steroids. Peripheral blood mononuclear cells (PBMCs) were obtained from patients with active inflammatory bowel disease (n=12). The age range was 20-51 (mean 28). Five women and seven men were studied, 5 patients with CD; 7 patients with UC.

Mesenteric lymph node cell (MLNC) isolation

Mesenteric lymph nodes (MLN) were selected for this study with careful regard to their anatomical location relative to areas of inflammation in the bowel. MLN selected directly drained an inflamed area of the bowel. From three patients within this study population, it was possible to obtain MLN draining segments of inflamed and non-inflamed bowel. Single cell suspensions were generated from MLN by gentle extrusion of the tissue through a 180μ mesh wire screen. Cells were washed and resuspended in DMEM (Dulbecco's modified eagle medium) containing 10% FCS (Invitrogen, Paisley, UK). Mononuclear cells were isolated by Ficoll-Hypaque density centrifugation and resuspended at $1\times10^6$ cells/ml in complete media—DMEM containing 25 mM glucose, 10% FCS, 1% nonessential amino acids, 50U/ml penicillin and 50 g/ml streptomycin (Invitrogen, Paisley, UK). These mononuclear cells are termed mesenteric lymph node cells (MLNCs).

Dendritic cell isolation

DCs from MLN and peripheral blood were isolated using identical procedures. Cells were resuspended at $5 \times 10^7$ cells/ml in PBS (without $Ca^{2+}$ or $Mg^{2+}$) with 4% FCS. For optimal recovery of DCs, 1 mM EDTA was added to all media and cell suspensions were blocked with anti-CD32 antibodies (Stem-Cell, Meylan, France). DCs were isolated from this cell suspension, according to the manufacturer's protocol, using a DC negative isolation kit (StemSep™ depletion cocktail, StemCell, Meylan, France). DCs were resuspended in Stemspan serum-free media (StemCell, Meylan, France) at $1 \times 10^6$ cells/ml. Viability, determined by trypan blue exclusion, was consistently $\geq 98\%$. Purity of DC preparations were assessed using flow cytometry. Cells which were HLA-DR positive and CD3/CD14/CD16/CD19/CD20/CD56 negative were termed DCs. All antibodies were obtained from BD Biosciences, (Oxford, UK).

Bacterial strains

We have previously reported the selection criteria for isolation of *Lactobacillus salivarius* UCC118 (*L. salivarius*) and *Bifidobacterium infantis* 35624 (*B. infantis*). *L. salivarius* and *B. infantis* were routinely cultured anaerobically for 24-48 hours in deMann, Rogosa and Sharpe medium, MRS, (Oxoid, Basingstoke, UK) and MRS supplemented with 0.05% cysteine (Sigma, Dublin, Ireland), respectively. *Salmonella typhimurium* UK1 (*S. typhimurium*) was cultured aerobically for 18-24 hours in tryptic soya broth (Oxoid, Basingstoke, UK). Bacterial cultures were harvested by centrifugation (3,000 g×15 mins), washed with PBS and subsequently diluted to form compositions comprising final cell densities of $1 \times 10^7$, $1 \times 10^5$ and $1 \times 10^3$ colony forming units (cfu)/ml in DMEM.

In vitro Treatment of Biological Sample

All cells were seeded in 24 well tissue culture plates (Costar, Schiphol-Rijk, Netherlands) at $1 \times 10^6$ cells/ml. MLNCs were stimulated for 72 hours with compositions comprising *L. salivarius*, *B. infantis* or *S. typhimurium* at 3 different bacterial concentrations, $1 \times 10^7$ CFU, $1 \times 10^5$ CFU and $1 \times 10^3$ CFU. As treatment with $1 \times 10^7$ bacteria resulted in significant stimulation of cytokine production, this bacterial concentration was used in subsequent experiments. MLNCs isolated from non-inflamed bowel were stimulated for 72 hours with these bacteria at $1 \times 10^7$ cfu. MLN-derived DCs were stimulated with *L. salivarius*, *B. infantis* or *S. typhimurium* for 24 hours. Untreated control biological samples were present to assess spontaneous levels of cytokine secretion. Plates were incubated in a 5% $CO_2$ and 37° C. humidified atmosphere after which supernatants were harvested for cytokine analysis. Cytokine production was measured, according to the manufacturer's instructions, using commercially available ELISA kits (R&D Systems, Abington, UK). Cytokines measured included TNF-α, IL-12 p40, IL-10 and TGF-β.

Statistical Analysis

Results were analysed using ANOVA analysis. Values are illustrated as the mean ±standard error mean. Statistically significant differences in cytokine production between non-stimulated cells (control) and cells stimulated with bacteria were accepted at $p < 0.05$.

Results

As can be seen from FIGS. 4, 5 and 6, the ratio of anti-inflammatory cytokines to pro-inflammatory cytokines produced by gut-derived cell types in vitro following stimulation with probiotic bacteria (Bif. 35624 and Lb. 118) is greater than the same ratio produced by non-stimulated control samples. This trend, whilst not always reaching statistical significance, is indicative of the different interaction probiotic compositions, and compositions in general that may be beneficial in the treatment of inflammatory diseases of the bowel, have on the gut tissues in vivo compared with that of pathogenic bacteria. This is believed to be indicative of the composition being an inhibitor of inflammatory diseases of the bowel. As can be seen from FIGS. 4, 5 and 6, stimulation with pathogenic bacteria (Salmonella) either results in no difference in the ratio of anti-inflammatory cytokines to pro-inflammatory cytokines when compared with the control, non-stimulated sample, or more typically, a reduction in said ratio. Again, whilst this difference does not always reach statistical significance, it is indicative of a composition that is not an inhibitor of inflammatory diseases of the bowel.

What is claimed is:

1. A method of determining the efficacy of a probiotic as a treatment of irritable bowel syndrome in mammals in vivo comprising the steps of:
    a) measuring the level of at least one anti-inflammatory cytokine selected from the group consisting of interleukin-10, transforming growth factor-β, interleukin-4, interleukin-5, interleukin-13, and combinations thereof and at least one pro-inflammatory cytokine selected from the group consisting of interleukin-12, tumour necrosis factor-α, interferon-γ, interleukin-2, and combinations thereof in a supernatant from cells cultured from a biological sample from a mammalian subject wherein said biological sample is selected from the group consisting of a biopsy sample from the bowel, peripheral blood mononuclear cells without in vitro stimulation, peripheral blood mononuclear cells with in vitro stimulation, gut lymphoid tissues without in vitro stimulation, gut lymphoid tissues with in vitro stimulation, and combinations thereof;
    b) determining the ratio of the level of the at least one anti-inflammatory cytokine to the level of the at least one pro-inflammatory cytokine;
    c) administering said treatment;
    d) measuring the level of the at least one anti-inflammatory cytokine and the at least one pro-inflammatory cytokine in a supernatant from cells cultured from a biological sample from said mammalian subject at a time following administration of said treatment;
    e) determining the ratio of the level of the at least one anti-inflammatory cytokine to the level of the at least one pro-inflammatory cytokine following administration of said treatment;

wherein an increase in the ratio of the levels of anti-inflammatory cytokine to pro-inflammatory cytokine following the administration of said treatment is indicative of the efficacy of said treatment for irritable bowel syndrome, and no change or a decrease in the ratio of the levels of anti-inflammatory to pro-inflammatory cytokine following the administration of said treatment is indicative of lack of efficacy of said treatment for irritable bowel syndrome.

2. The method according to claim 1 wherein the anti-inflammatory cytokine is selected from the group consisting of interleukin-10, transforming growth factor-β, and combinations thereof.

3. The method according to claim 1 wherein the pro-inflammatory cytokine comprises interleukin-12, tumour necrosis factor-α, interferon-γ, or combinations thereof.

4. The method according to claim 1, wherein said ratio of the level of anti-inflammatory cytokine to pro-inflammatory cytokine is the ratio of the level of interleukin-10 to the level of interleukin-12.

5. The method according to claim 1, wherein said ratio of the level of anti-inflammatory cytokine to pro-inflammatory cytokine is the ratio of the level of transforming growth factor-β to the level of interleukin-12.

6. The method according to claim 1, wherein said ratio of the level of anti-inflammatory cytokine to pro-inflammatory cytokine is the ratio of the level of interleukin-10 to the level of interferon-γ.

7. The method according to claim 1 wherein said biological sample comprises peripheral blood mononuclear cells with in vitro stimulation, peripheral blood mononuclear cells without in vitro stimulation, or combinations thereof.

8. The method according to claim 1 wherein said in vitro stimulation comprises stimulation with a mitogen, a probiotic, an anti-CD3 molecule, or combinations thereof.

9. The method according to claim 8, wherein said in vitro stimulation comprises stimulation with a mitogen.

10. The method according to claim 9 wherein said mitogen comprises a lipopolysaccharide, lectin, superantigen, or combinations thereof.

11. The method according to claim 10, wherein said lectin comprises concanavalin A, phytohemagglutinin, pokeweed mitogen, or combinations thereof.

12. The method according to claim 1 further comprising a means for measuring the levels of said at least one anti-inflammatory cytokine in said biological sample, wherein said means measures mRNA or protein expression and comprises ELISAs, radioimmunoassays, multiplexed ELISAs on microarray platforms, multiplexed ELISAs using coded microspheres coupled with a flow cytometer detection systems, bioassays, Western blots, chromatograph-based separation systems, RT-PCR, competitive reverse transcription PCR, Northern blots, gene arrays, direct measurement of m-RNA, or combinations thereof.

13. The method according to claim 12 wherein the means for measuring the levels of anti-inflammatory cytokines in said biological sample comprises ELISAs, RIAs, multiplexed ELISAs using coded microspheres coupled with a flow cytometer detection systems, or combinations thereof.

14. The method according to claim 13 wherein the means for measuring the levels of said at least one anti-inflammatory cytokine in said biological sample comprises multiplexed ELISAs using coded microspheres coupled with a flow cytometer detection system.

15. The method according to claim 1 further comprising a means for measuring the levels of said at least one pro-inflammatory cytokine in said biological sample, wherein said means measures mRNA or protein expression and comprises ELISAs, radioimmunoassays, multiplexed ELISAs on microarray platforms, multiplexed ELISAs using coded microspheres coupled with a flow cytometer detection systems, bioassays, Western blots, chromatograph-based separation systems, RT-PCR, competitive reverse transcription PCR, Northern blots, gene arrays, direct measurement of m-RNA, or combinations thereof.

16. The method according to claim 15 wherein the means for measuring the levels of said at least one pro-inflammatory cytokine in said biological sample comprises ELISAs, RIAs, multiplexed ELISAs using coded microspheres coupled with a flow cytometer detection systems, or combinations thereof.

17. The method according to claim 16, wherein the means for measuring the levels of said at least one pro-inflammatory cytokine in said biological sample comprises multiplexed ELISAs using coded microspheres coupled with a flow cytometer detection system.

18. A method of determining the efficacy of a probiotic as a treatment of irritable bowel syndrome in humans in vivo comprising the steps of:
  f) measuring the level of at least one anti-inflammatory cytokine selected from the group consisting of interleukin-10, transforming growth factor-β, interleukin-4, interleukin-5, interleukin-13, and combinations thereof and at least one proinflammatory cytokine selected from the group consisting of interleukin-12, tumour necrosis factor-α, interferon-γ, interleukin-2, and combinations thereof in a supernatant from cells cultured from a biological sample from a human subject wherein said biological sample is selected from the group consisting of a biopsy sample from the bowel, peripheral blood mononuclear cells without in vitro stimulation, peripheral blood mononuclear cells with in vitro stimulation, gut lymphoid tissues without in vitro stimulation, gut lymphoid tissues with in vitro stimulation, and combinations thereof;
  g) determining the ratio of the level of the at least one anti-inflammatory cytokine to the level of the at least one pro-inflammatory cytokine;
  h) administering said treatment;
  i) measuring the level of the at least one anti-inflammatory cytokine and the at least one pro-inflammatory cytokine in a supernatant from cells cultured from a biological sample from said human subject at a time following administration of said treatment;
  j) determining the ratio of the level of the at least one anti-inflammatory cytokine to the level of the at least one pro-inflammatory cytokine following administration of said treatment;
  wherein an increase in the ratio of the levels of anti-inflammatory cytokine to pro- inflammatory cytokine following the administration of said treatment is indicative of the efficacy of said treatment for irritable bowel syndrome, and no change or a decrease in the ratio of the levels of anti-inflammatory to pro-inflammatory cytokine following the administration of said treatment is indicative of lack of efficacy of said treatment for irritable bowel syndrome.

19. The method according to claim 18, wherein said ratio of the level of anti-inflammatory cytokine to pro-inflammatory cytokine is the ratio of the level of interleukin-10 to the level of interleukin-12.

20. The method according to claim 18, wherein said ratio of the level of anti-inflammatory cytokine to pro-inflammatory cytokine is the ratio of the level of transforming growth factor-β to the level of interleukin-12.

21. The method according to claim 18, wherein said ratio of the level of anti-inflammatory cytokine to pro-inflammatory cytokine is the ratio of the level of interleukin-10 to the level of interferon-γ.

* * * * *